US008376803B2

(12) United States Patent
Oonaka

(10) Patent No.: US 8,376,803 B2
(45) Date of Patent: Feb. 19, 2013

(54) CHILD-CARE ROBOT AND A METHOD OF CONTROLLING THE ROBOT

(75) Inventor: Shinichi Oonaka, Tokyo (JP)

(73) Assignee: NEC Corporation, Tokyo (JP)

( * ) Notice: Subject to any disclaimer, the term of this patent is extended or adjusted under 35 U.S.C. 154(b) by 2094 days.

(21) Appl. No.: 11/089,433

(22) Filed: Mar. 25, 2005

(65) Prior Publication Data
US 2005/0215171 A1 Sep. 29, 2005

(30) Foreign Application Priority Data

Mar. 25, 2004 (JP) ................................ 2004-088734
Aug. 11, 2004 (JP) ................................ 2004-234890

(51) Int. Cl.
A63H 30/00 (2006.01)
G06F 19/00 (2006.01)
(52) U.S. Cl. ........ 446/175; 446/484; 700/245; 700/257; 379/38
(58) Field of Classification Search .................. 446/175; 700/245–247, 257; 379/37–38, 42; 434/236, 434/238; A63H 30/00; G06F 19/00
See application file for complete search history.

(56) References Cited

U.S. PATENT DOCUMENTS

| 6,175,772 | B1 * | 1/2001 | Kamiya et al. .................. 700/31 |
| 6,352,478 | B1 * | 3/2002 | Gabai et al. ...................... 463/42 |
| 2002/0161480 | A1 * | 10/2002 | Kakutani et al. ............... 700/245 |
| 2002/0177925 | A1 * | 11/2002 | Onishi et al. ................... 700/245 |
| 2002/0183598 | A1 * | 12/2002 | Teraura et al. ................. 600/300 |
| 2003/0182117 | A1 * | 9/2003 | Monchi et al. ................. 704/237 |
| 2004/0162637 | A1 * | 8/2004 | Wang et al. .................... 700/245 |
| 2009/0124165 | A1 * | 5/2009 | Weston .......................... 446/268 |

FOREIGN PATENT DOCUMENTS

| JP | 2000-353012 | 12/2000 |
| JP | 2001-157985 | 6/2001 |
| JP | 2001-246580 | 9/2001 |
| JP | 2002-73634 | 3/2002 |
| JP | 2002-127059 | 5/2002 |
| JP | 2003-291084 | 10/2003 |
| JP | 2004-357915 | 12/2004 |
| JP | 2006-39760 | 2/2006 |
| JP | 2009-297892 | 12/2009 |

OTHER PUBLICATIONS

Japanese Office Action with English translation.

* cited by examiner

Primary Examiner — Dmitry Suhol
Assistant Examiner — Alex F. R. P. Rada, II
(74) Attorney, Agent, or Firm — Whitham Curtis Christofferson & Cook, PC

(57) ABSTRACT

A child-care robot for use in a nursery school associates child behavior patterns with corresponding robot action patterns, and acquires a child behavior pattern when a child behaves in a specified pattern. The robot selects one of the robot action patterns, which is associated with the acquired child behavior pattern, and performs the selected robot action pattern. Additionally, the robot associates child identifiers with parent identifiers, and receives an inquiry message from a remote terminal indicating a parent identifier. The robot detects one of the child identifiers, which is associated with the parent identifier of the inquiry message, acquires an image or a voice of a child identified by the detected child identifier, and transmits the acquired image or voice to the remote terminal. The robot further moves in search of a child, measures the temperature of the child, and associates the temperature with time of day at which it was measured.

26 Claims, 14 Drawing Sheets

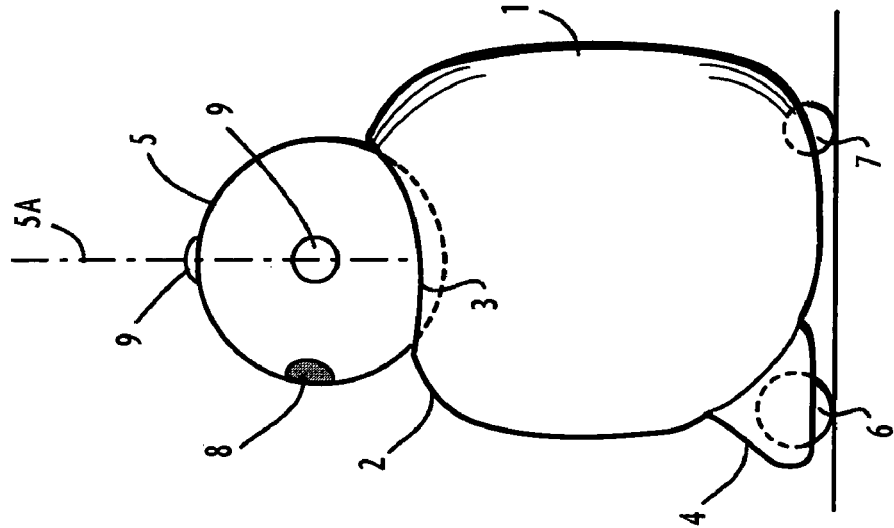
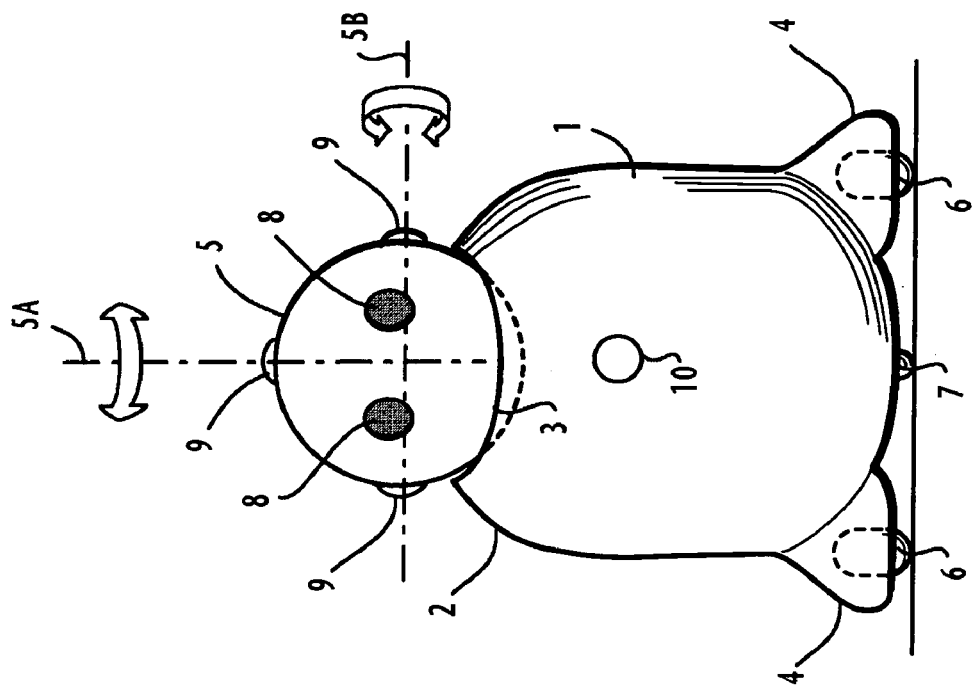

FIG. 5

PARENTS DATA MEMORY

| PARENTS NAME | PARENTS ID | PASSWORD | ADDRESS | MEANS OF COMM. | CHILD ID | CHILD NAME |
|---|---|---|---|---|---|---|
| | | | | E-MAIL | | |
| | | | | PHONE NO. | | |
| | | | | PHONE NO. | | |
| ⋮ | ⋮ | ⋮ | ⋮ | ⋮ | ⋮ | ⋮ |
| | | | | | | |

FIG. 6

ACTION PATTERN MEMORY

| VOICE PATTERN | ACTION (1) | ACTION (2) |
|---|---|---|
| WEEPING | NOTIFY PARENTS | NOTIFY TEACHERS |
| SCREAMING | NOTIFY TEACHERS | LOUDLY ANNOUNCE |
| ⋮ | ⋮ | ⋮ |
| | | |

CHILD-CARE ROBOT AND A METHOD OF CONTROLLING THE ROBOT

BACKGROUND OF THE INVENTION

1. Field of the Invention

The present invention relates generally to robots, and more specifically to a child-care robot and a method of controlling a child-care robot. The present invention is particularly useful as a playmate for young children as well as an aid for teachers in nursery schools or the like.

2. Description of the Related Art

In modern society, there are an increasing number of working parents whose concern is on raising their families, particularly their young children. Nursery schools are becoming a social need. However, the number of public and private nursery schools is not sufficient in some local areas and reducing the number of non-admitted children to zero has become a public issue of the areas. The problem hinges on the personnel expenditure of nursery school teachers which accounts for a greater portion of the running cost of nursery school.

Recent advances in microprocessors and robotics have culminated in the development of two-footed robots known under the trade names of "Aibo" and "Asimo". These robots are playmate robots, not dedicated to perform a particular assignment, such as child care.

Japanese Patent Publication 2000-353012 discloses a robot for nursing the aged or the handicapped. The robot has an eye whose viewing point is determined with respect to the position of a user. In response to a voice command from the user, the robot interprets the voice command at the determined viewing point and determines its direction of motion.

However, the prior art playmate and nursing robots are unsatisfactory to meet the need of reducing the personnel expenditure of nursery schools.

SUMMARY OF THE INVENTION

It is therefore an object of the present invention to provide a child-care robot and a method of controlling a child-care robot, which can be used as an aid for nursery school teachers to reduce their burden of child care and hence their personnel expenditure.

According to a first aspect of the present invention, there is provided a child-care robot comprising memory means for associating a plurality of child behavior patterns with a plurality of robot action patterns, sensor means for acquiring child behavior pattern when a child behaves in a specified pattern, processor means for selecting one of the robot action patterns which is associated in the memory means with the acquired child behavior pattern, and acting means for performing the selected robot action pattern.

According to a second aspect, the present invention provides a child-care robot comprising memory means for associating a plurality of child identifiers with a plurality of parent identifiers, communication means for receiving an inquiry message from a remote terminal indicating a parent identifier, processor means for detecting one of the child identifiers which is associated with the parent identifier of the inquiry message, and sensor means for acquiring an image or a voice of a child identified by the detected child identifier. The communication means transmits the acquired image or voice to the remote terminal.

According to a third aspect, the present invention provides a child-care robot comprising acting means for moving the robot around until a target child is identified, temperature measuring means for measuring the temperature of the identified child, and memory means for associating the measured temperature of the identified child with data indicating time of day at which the temperature is measured.

According to a fourth aspect, the present invention provides a child-care robot comprising acting means for moving the robot around an area in search of a plurality of objects and detecting a plurality of geographic positions of the objects, memory means for associating the detected geographic positions of objects with a plurality of identities of the objects, and processor means for creating a map for indicating the geographic positions of the objects and the identities of the objects on a floor layout of an architecture.

According to a fifth aspect of the present invention, there is provided a method of controlling a child-care robot, comprising associating a plurality of child behavior patterns with a plurality of robot action patterns, acquiring a child behavior pattern when a child behaves in a specified pattern, selecting one of the robot action patterns which is associated with the acquired child behavior pattern, and performing the selected robot action pattern.

According to a sixth aspect, the present invention provides a method of controlling a child-care robot, comprising associating a plurality of child identifiers with a plurality of parent identifiers, receiving an inquiry message from a remote terminal indicating a parent identifier, detecting one of the child identifiers which is associated with the parent identifier of the inquiry message, acquiring an image or a voice of a child identified by the detected child identifier, and transmitting the acquired image or voice to the remote terminal.

According to a seventh aspect the present invention provides a method of controlling a child-care robot, comprising moving the robot around until a target child is identified, measuring the temperature of the identified child, and associating the measured temperature of the identified child with data indicating time of day at which the temperature is measured.

According to a further aspect of the present invention, there is provided a method of controlling a child-care robot, comprising moving the robot around an area in search of a plurality of objects and detecting a plurality of geographic positions of the objects, associating the detected geographic positions of objects with a plurality of identities of the objects, and creating a map for indicating the geographic positions of the objects and the identities of the objects on a floor layout of an architecture.

BRIEF DESCRIPTION OF THE DRAWINGS

The present invention will be described in detail further with reference to the following drawings, in which:

FIGS. 1A and 1B are front and side views of a child-care robot of the present invention, respectively;

FIG. 5 is an illustration of the parents data memory of FIG. 4;

FIG. 6 is an illustration of the action pattern memory of FIG. 4;

DETAILED DESCRIPTION

Figure 2:
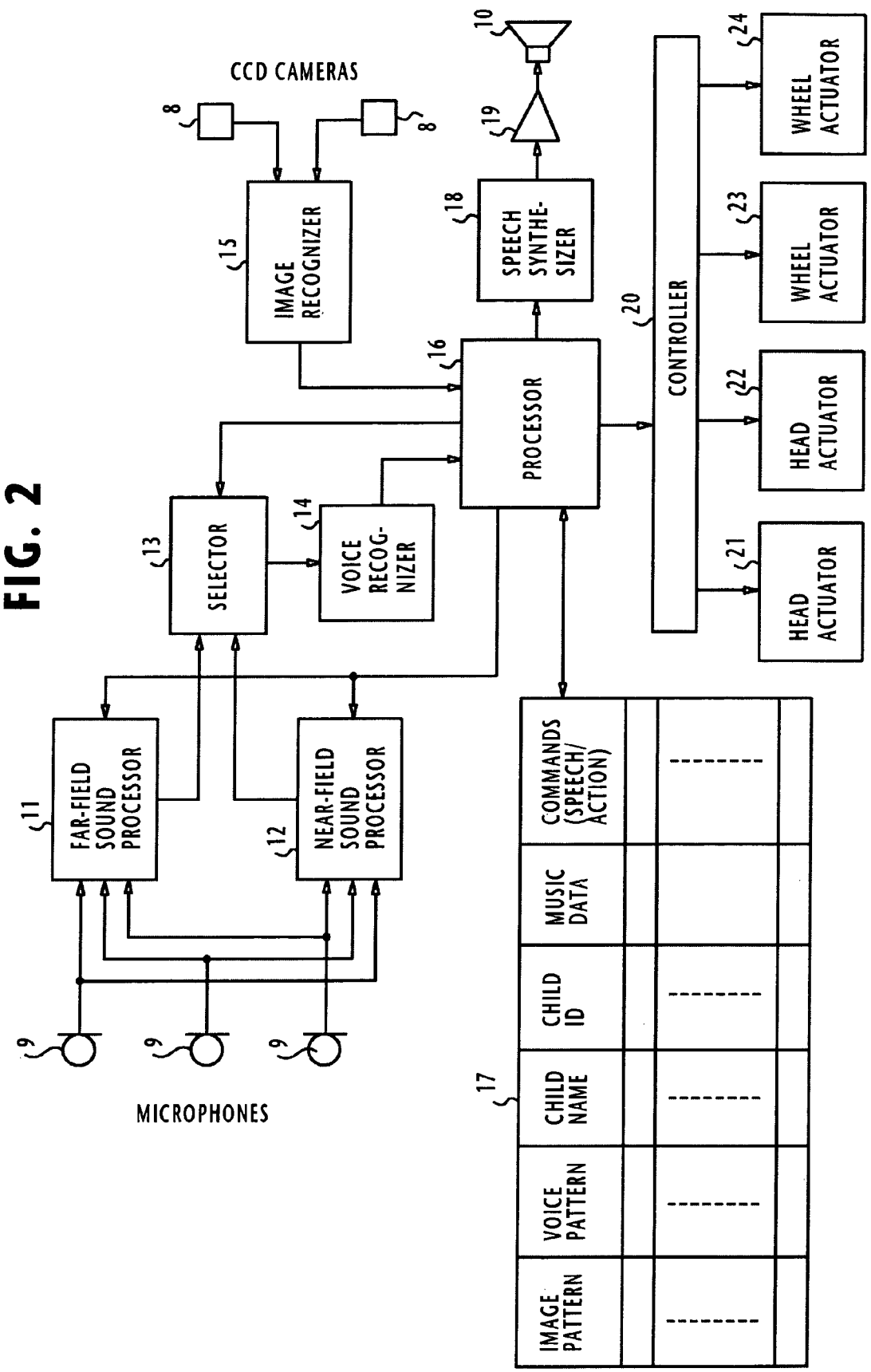
FIG. 2 is a block diagram of the child-care robot according to a first embodiment of the present invention.

In FIGS. 1A and 1B, a child-care robot of the present invention is illustrated. The robot comprises a torso 1 of generally cylindrical shape with a rounded upper portion 2 having a circular opening 3 and a pair of limb portions 4 on its front side. A head 5 of spherical shape is partially submerged in the opening 3 and rotatably secured so that it can orient its face in a limited horizontal angle about a vertical axis 5A and in a limited vertical angle about a horizontal axis 5B. Each of the limb portions 4 extends outwards from the torso 1 and includes a driven wheel 6. A castor 7 is fitted to the bottom of torso 1 near its rear side so that the robot is capable of moving about in a nursery school or the like.

Head 5 is provided with a pair of CCD cameras 8 in the positions of eyes and an array of microphones 9, one at the top of head 5 and two in the positions of ears. A loudspeaker 10 is provided on the front side of torso 1.

A first embodiment of the robot is shown in FIG. 2. As illustrated, the robot includes a far-field sound processor 11 and a near-field sound processor 12 connected to the microphones 9, and an image recognizer 15 connected to the CCD cameras 8. A selector 13 is provided for selecting one of the outputs of sound processors 11, 12 according to the output of a processor 16 and supplies its output to a voice recognizer 14. Processor 16 is responsive to the outputs of voice recognizer 14 and image recognizer 15 to consult a pattern memory 17 to take an appropriate robot action. The output signal of the processor 16 is coupled either to a speech synthesizer 18 or a controller 20 or both. The output of speech synthesizer 18 is supplied through an amplifier 19 to the loudspeaker 10 to produce a synthesized human voice.

The robot includes a pair of head actuators 21 and 22 for respectively controlling the orientation of the head 5 in vertical and horizontal angular positions and a pair of wheel actuators 23 and 24 for moving the robot in a specified direction. Controller 20 responds to the output signal from the processor 16 to individually control these actuators. Processor 16 includes a CPU 25 and a ROM 26 that stores a control program to be performed by the CPU 25.

Far-field sound processor 11 selectively uses one of the microphones 9 to detect undesired noise and uses an adaptive filter to suppress the noise contained in the input signals from all microphones. Near-field sound processor 12 performs an adaptive array processing on the input signals from all microphones to emphasize the voice arriving in a particular direction. This accentuates a particular voice, which may occur when a child is crying (such a case is of primary concern for child care). When the processor 16 determines that the image recognizer 15 does not detect a target child in an area close to the robot, the processor commands the selector 13 to select the output of far-field sound processor 11. Otherwise, the processor 16 commands the selector 13 to select the output of near-field sound processor 12.

In the pattern memory 17, input image (facial) and voice patterns of all children of the nursery school are mapped to their names and identification numbers, music data and commands (including speech and action). In one application, each child wears an identification tag (such as wireless IC tag) and the robot is provided with a wireless tag reader for detecting the child identification number it carries. Processor 16 compares the detected child identification number to all child identification numbers stored in the pattern memory 17 for a match to find the name of the child. Images of various 3D objects and their names may also be stored in the memory 17.

In response to a given behavior of a child, the processor 16 is supplied with a speech pattern of the child from the voice recognizer 14 and a facial image pattern of the child from the image recognizer 15. Using the input patterns as a search key, the processor 16 selects an action from the pattern memory 17 to take care of the child. Depending on the timing the processor 16 is supplied with the input patterns from the recognizers 14 and 15, the processor 16 randomly selects a piece of music from the pattern memory 17 to entertain children.

Using the recognized image and voice patterns and the pattern memory 17, the processor 16 is able to recognize the presence of a child near the robot or locate the position of a target child or identify a child by name and identification number. In response to an input voice pattern from the voice recognizer 14 or an input image pattern from the image recognizer 15, the processor 16 makes fa search through the pattern memory 17 for a corresponding action and/or a corresponding speech pattern. The detected action is supplied to the controller 20 where it is converted to a set of drive signals for selectively operating the actuators. The detected speech pattern is supplied to the speech synthesizer 18 where it is converted to a synthesized human voice.

Figure 3:
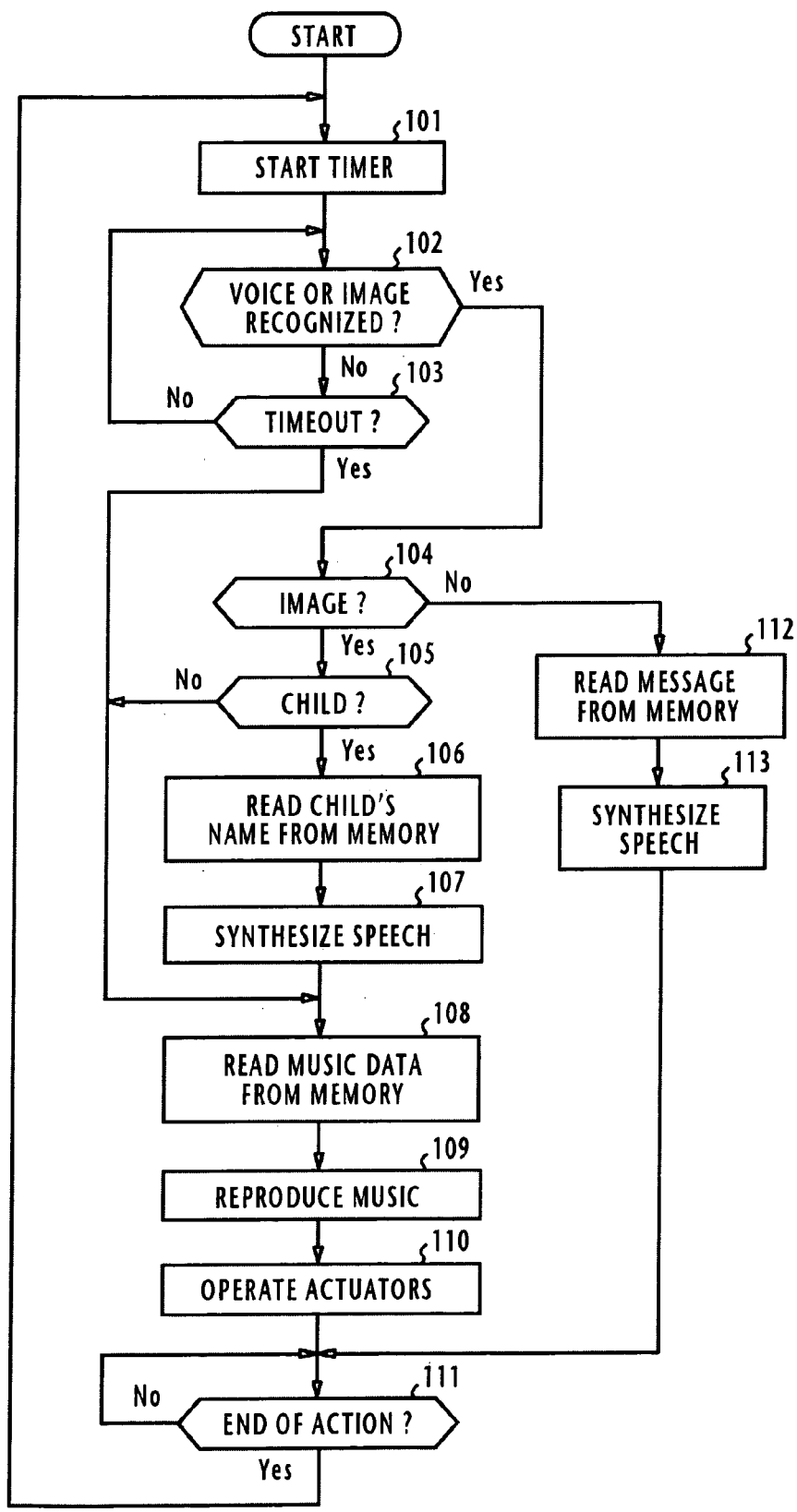
FIG. 3 is a flowchart of the operation of the processor of FIG. 2.

The operation of the robot of FIG. 2 proceeds according to the flowchart of FIG. 3.

The operation begins with step 101 to start a timer and flow proceeds to decision step 102. If no image or voice input pattern is detected, flow proceeds to step 103 to check to see if the time has run out. If not, flow returns to step 102 to monitor the input voice and image patterns.

If an image or a voice input pattern is recognized (step 102) and the recognized input is image (step 104), flow proceeds to step 105 to determine if the input image is the image of a child. If so, flow proceeds to step 106 to make a search through the pattern memory 17 for a child's name corresponding to the input image pattern (additionally using the wireless ID tag of the child). By uttering the child's name, the child's attention is drawn to the robot with a sense of affinity.

At step 107, the child's name is synthesized and reproduced by the speaker 10. As a robot action, music data is read from the pattern memory (step 108) and a piece of music is randomly selected from the retrieved music data and reproduced (step 109) and the wheel actuators and/or the head actuators are operated (step 110) to move the robot around and/or wobble the head in vertical direction in tune to the music in a playful manner.

If no child image is detected at step (105), steps 108 to 110 are executed. When the robot action terminates (step 111), flow returns to step 101 to repeat the process.

If the recognized input is a voice pattern (such as "Hello"), flow proceeds from step 104 to step 112 to make a search through the pattern memory 17 for a message speech pattern (such as "Good Morning") corresponding to the input voice pattern. If such a speech pattern is detected, it is read from the pattern memory 17 as a robot action and synthesized for utterance from the speaker 10 (step 113). The uttered message is one that is responsive to the child's input voice, giving an impression that the child is talking to the teacher. Thus, the robot is acting as if it were a nursery school teacher. When the message has been uttered, and no more robot action exists for the input voice (step 111), flow returns to step 101 to repeat the process.

If the timer has run out, the decision at step 103 is affirmative and flow proceeds to step 108 to read music data and randomly select a piece of music, reproduce it (step 109) and operate appropriate actuators in tune to the music (step 110). As a result, if there is no voice or image input for a period of 10 seconds, for example, the robot reproduces music and moves itself in a playful manner. If this absence-of-input condition persists, different music will be selected at random at 10-second intervals and played back to entertain children. This reduces the burden on the nursery school teachers with a possibility that their personal expenditures can be reduced.

Figure 4:
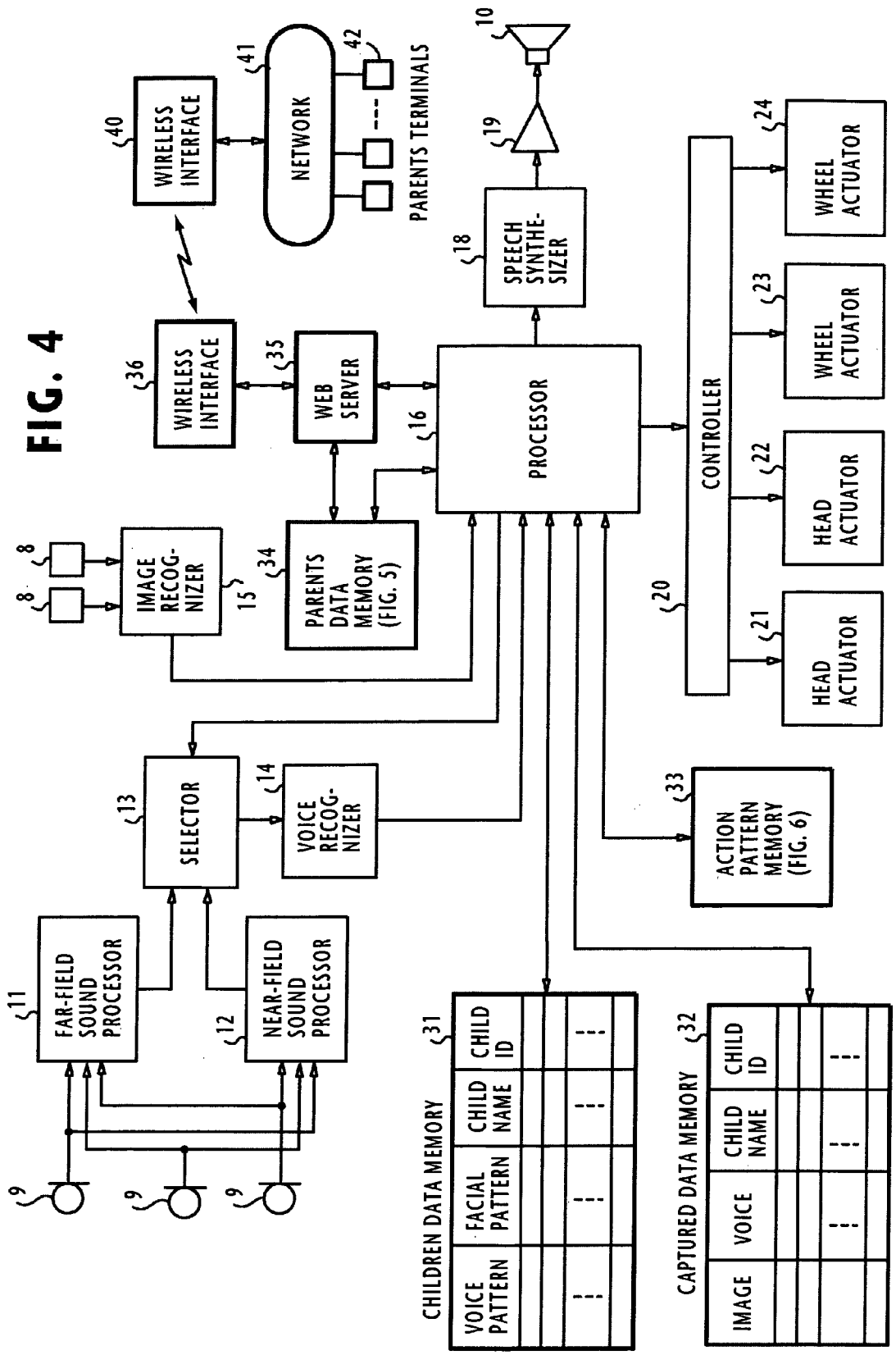
FIG. 4 is a block diagram of the child-care robot according to a second embodiment of the present invention.

A second embodiment of the robot is shown in FIG. 4 in which part corresponding in significance to those of FIG. 2 are marked with same numerals and the description thereof is omitted.

In FIG. 4, instead of the pattern memory 17 of FIG. 2, a children data memory 31, a captured data memory 32, an action pattern memory 33 and parents data memory 34 are provided. The robot further includes a web server 35, which is connected between the processor 16 and a wireless interface 36. The latter establishes a wireless link with a stationary wireless interface 40 located in a fixed position with respect to the robot. Wireless interface 40 is connected to a communications network 41 (such as public switched telephone network, mobile communication network, or IP network) through which the web server 35 of the robot can communicate with parents HTTP terminals 42.

Children data memory 31 contains a plurality of fields (columns) for mapping different voice patterns and different facial patterns of each child to the name and ID of the child. Captured data memory 32 stores a captured facial expression and voice of children in association with their name and identification number.

As shown in FIG. 5, for each parent entry, the parents data memory 34 includes a plurality of fields (columns) for storing parent name, parent ID, password, address, means of communication (such as e-mail, mobile and fixed phone numbers), child ID and child name.

Web server 35 is connected to the parents data memory 34. When an inquiry message is received from the terminal 42 of a child's parent through the wireless interface 36, the web server 35 searches the parents data memory 34 for a child identification number contained in the corresponding parent entry and asks the requesting terminal to send a password for verification. If the web server verifies the received password, it allows the received inquiry message to be passed on to the processor 16.

As shown in FIG. 6, the action pattern memory 33 specifies different robot actions to be taken in response to different voice patterns of each child. The voice patterns include crying, laughter, yelling and so on. Action (1) is taken first and action (2) is taken subsequently. For a weeping voice pattern, the action (1) includes an action to "notify" parents, and action (2) includes an action to "notify teachers". If a child screams, the action (1) notifies the teachers and an alarm is generated in the action (2).

Figure 7:
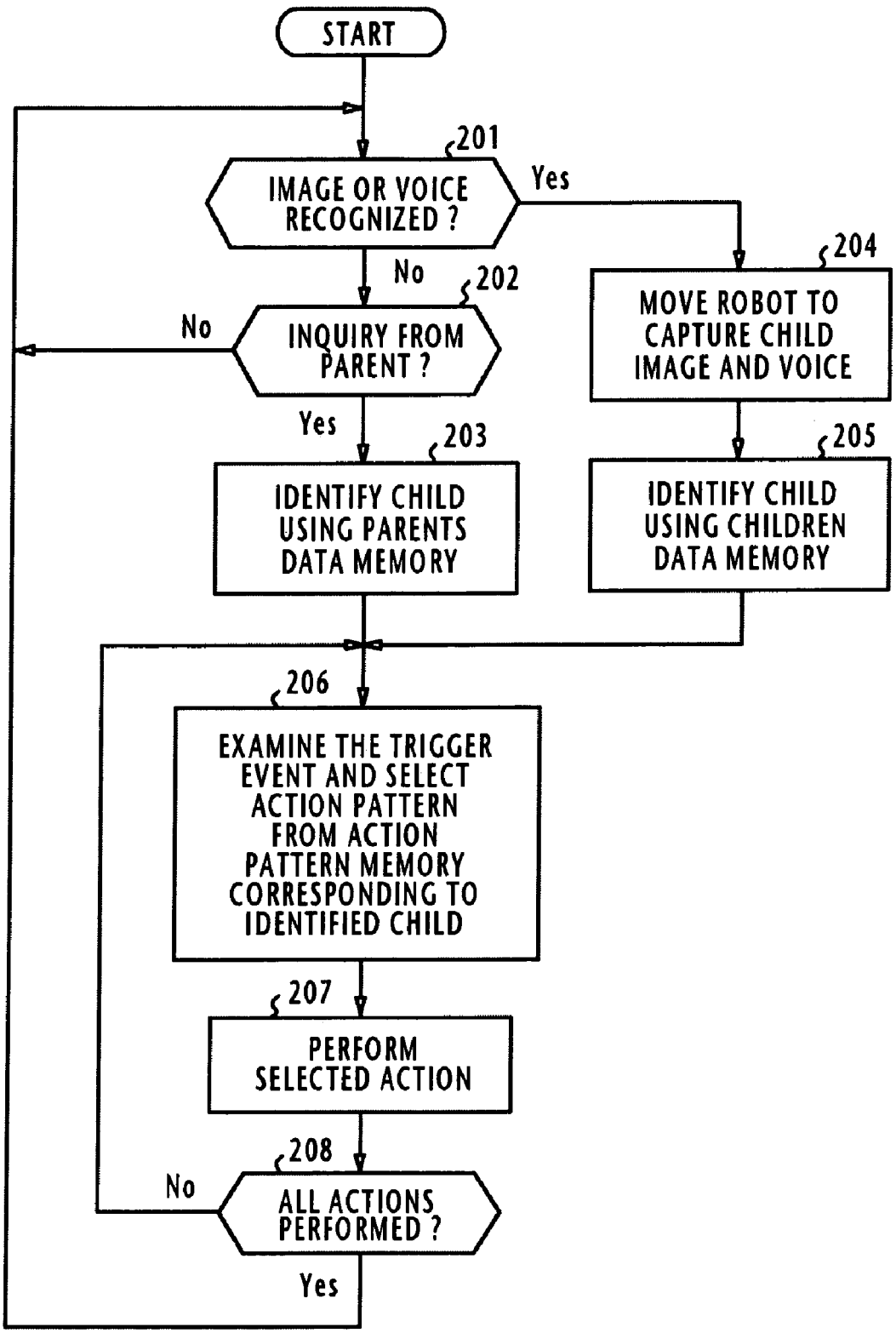
FIG. 7 is a flowchart of the operation of the processor of FIG. 4.

The operation of the robot of FIG. 4 proceeds according to the flowchart of FIG. 7. When the robot encounters a trigger event such as the recognition of an input image or voice pattern (step 201) or the receipt of an inquiry message from a parent terminal 42 (step 202). If an inquiry message is received from the web server 35, flow proceeds to step 203 to search the parents data memory 34 for the identification number of the child of the requesting terminal 42. At step 206, the processor 16 analyzes the trigger event and makes a search through the action pattern memory 33 for selecting an action to be taken for the identified child depending on the trigger event. The selected action is then performed (step 207). When all actions to be taken are successfully performed (step 208), flow returns to step 210 to repeat the process. Otherwise, flow returns from step 208 to step 206 to select the next action.

In case the trigger event is an inquiry message from a parent and the message is expressing a concern that requests the transmission of a most recent picture of the child, the selected action may take the form of reading a picture from the captured data memory 32 and replying the inquiry message with an e-mail with the retrieved picture as an attached document. Alternatively, the processor 16 sends the retrieved picture to a Web site and informs the requesting terminal of the URL of the Web site with a message indicating that accessing that Web site enables the parent to browse the child's picture. If the inquiry message requests the robot to transmit a real-time video image of the child, the selected action may take the form of operating the wheel actuators to move the robot around in search of the identified child. When the identified child is located, the processor captures the video image of the child and the child's voice using the CCD cameras 8 and the microphones 9 and sends them to the requesting terminal.

In case the trigger event is a recognized image or voice pattern of a child, the processor 16 proceeds to step 204 to move the robot to the location where the child is, captures the image and voice of the child and stores the captured data into the captured data memory 32. At step 205, the processor 16 makes a search through the children data memory 31 for a corresponding child identification number. At step 206, a search is made through the action pattern memory 35 for a voice pattern that matches the output of voice recognizer 14. Then, a pattern of action is selected from the action pattern memory 35 corresponding to the matched voice pattern.

If the matched voice pattern is the weeping pattern of a child, the first action to be taken is to transmit the captured image of the child to the parent's terminal 42. If the first action fails to capture the image of the weeping child or fails to receive a response from the parent due to some transmission error, the second action is taken. In the second action, the processor operates the wheel actuators to move the robot to a place near the teacher's room to loudly announce the child's unfavorable condition. The first action can be modified such that the parents are informed of this event if the child continues weeping for a predetermined period of time.

If the matched voice pattern is the screaming pattern, the first action is to move the robot to the teacher to inform the teacher of the name of the screaming child. If the first action fails to locate the teacher, the second action is to generate an alarm announcing that "a child is screaming" while moving about in the nursery school to ask for a helping hand.

In a modified embodiment, a teacher data memory is additionally included for mapping the teachers' voices and facial images to their names and identification numbers and further to children cared for by the teachers. The teacher data memory is used during a search for the teacher who is in charge of the weeping child.

In a further modified embodiment, a wireless microphone is attached to each child and the robot is equipped with a wireless receiver to detect signals from all wireless microphones. Each wireless microphone includes a digital circuit that transmits the unique identification code of the microphone to the robot to allow the processor 16 to identify each microphone. The identification codes of all wireless microphones are mapped in the children data memory 31 to the entry of the child wearing the microphone. By making a search through the children data memory 31 for a corresponding microphone identification code, child's behaviors can be correctly identified.

Figure 8:
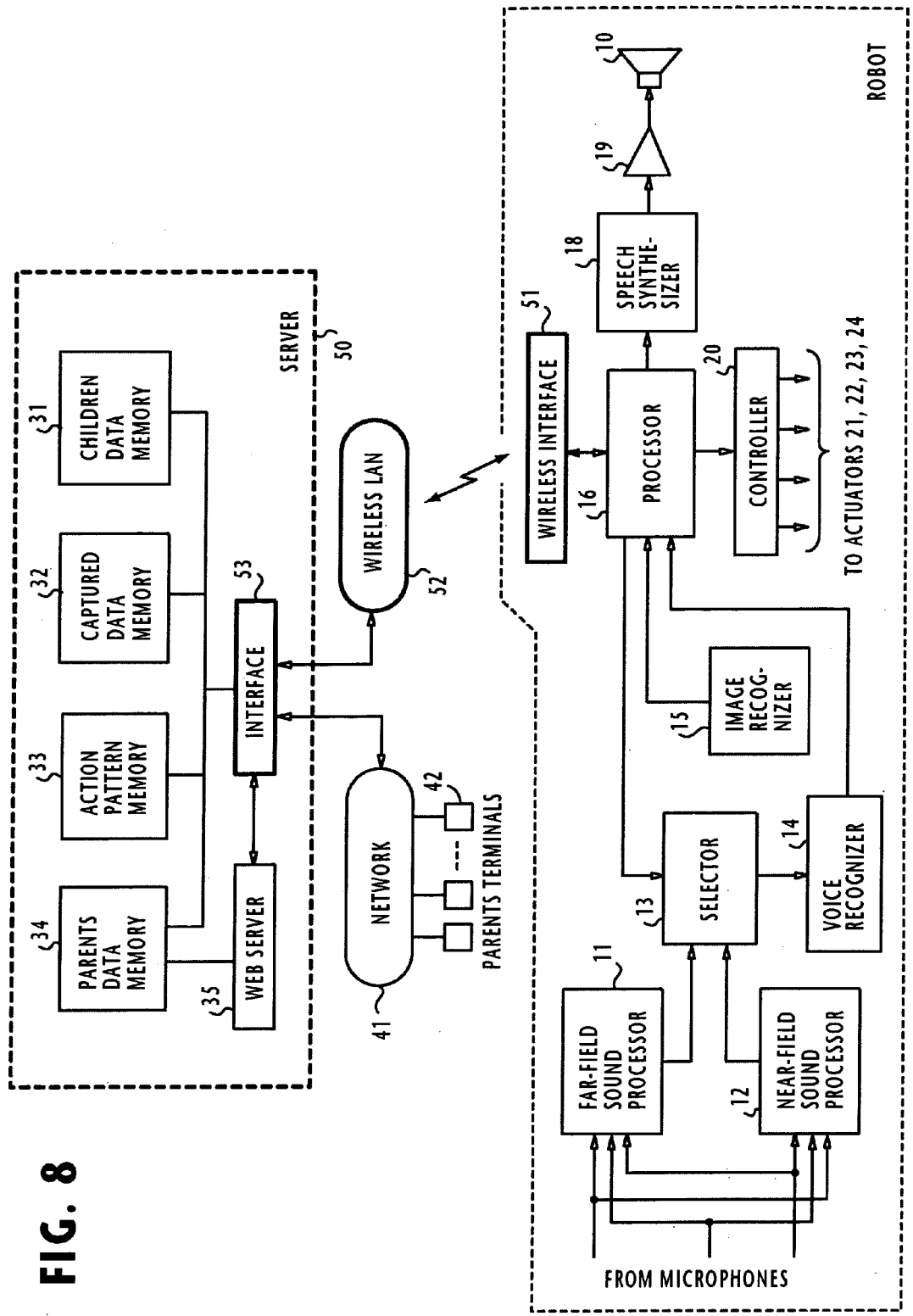
FIG. 8 is a block diagram of the child-care robot according to a modified embodiment of the present invention.

In an alternative embodiment, a child-care server 50 is provided as shown in FIG. 8. In this embodiment, the children data memory 31, captured data memory 32, action pattern memory 33, parents data memory 34 and the Web server 35 of the previous embodiment are removed from the robot to the child-care server 50. The robot includes a wireless interface 51, which is connected to the processor 16 interfaces between the robot and a wireless LAN 52. Child-care server 50 is provided with an interface 53 to which the memories 31 to 34 and the Web server 35 are connected. Interface 53 establishes connection between the network 41 and the wireless LAN 52.

Figure 9:
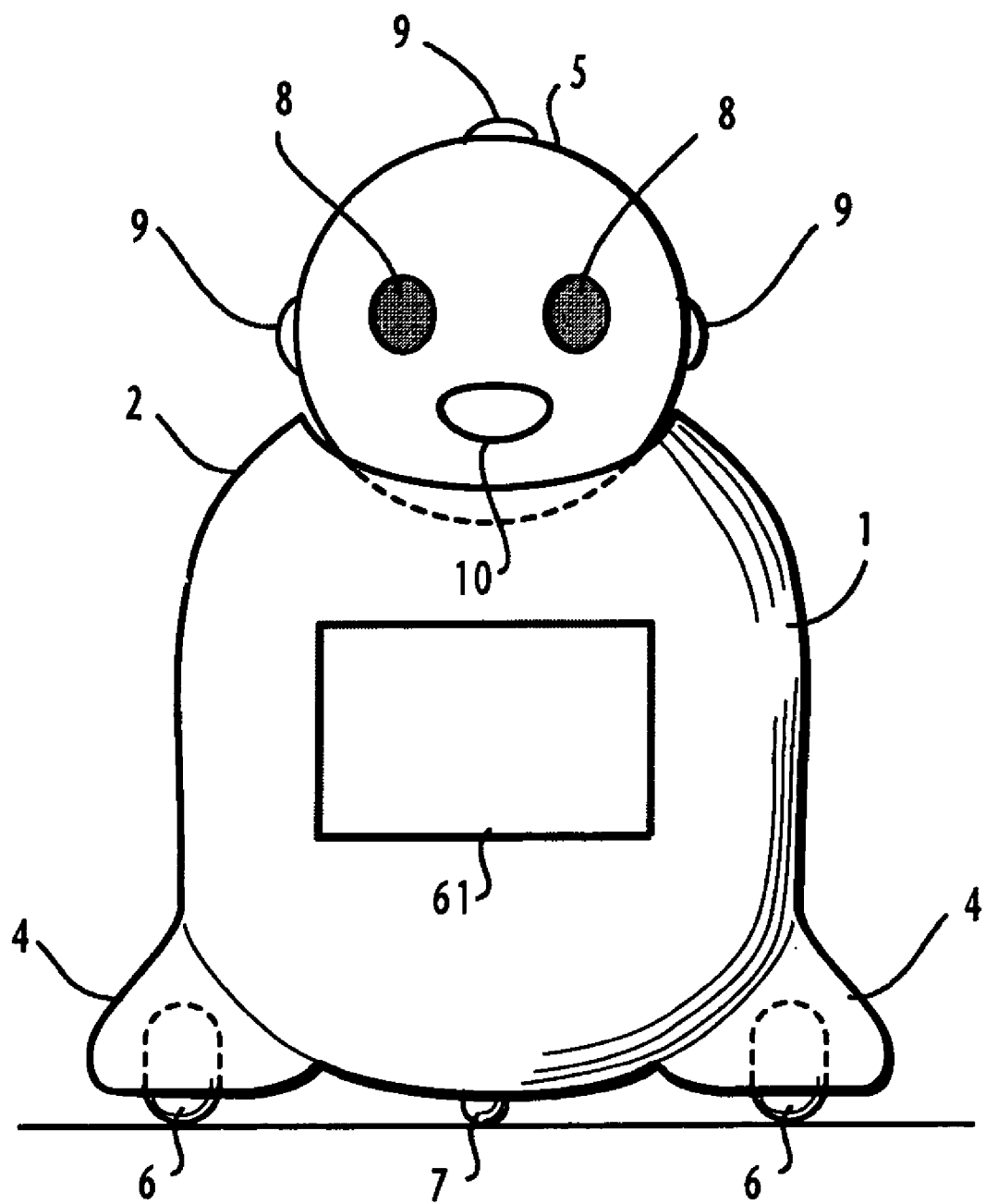
FIG. 9 is a front view of the child-care robot according to a third embodiment of the present invention.
Figure 10:
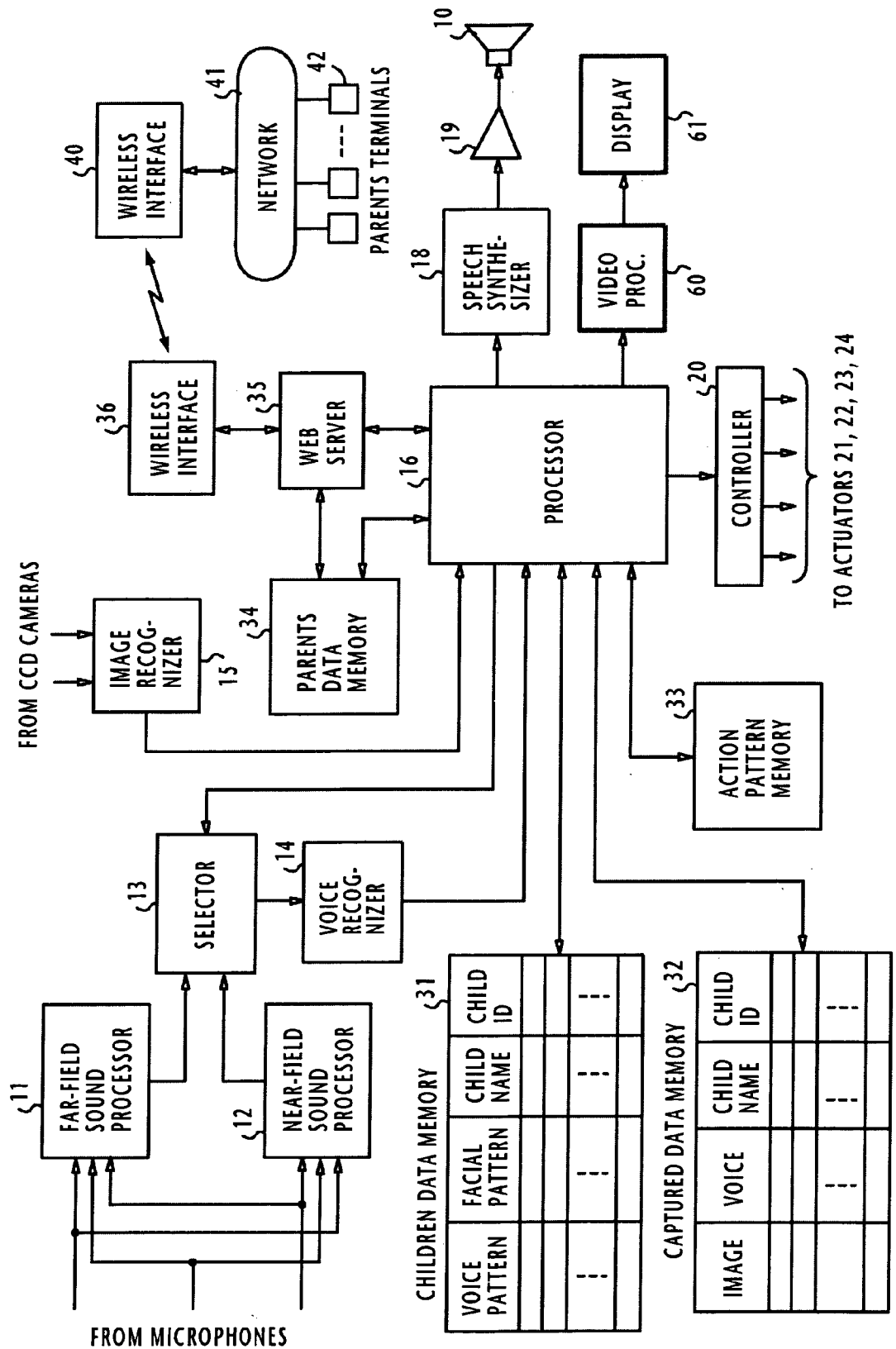
FIG. 10 is a block diagram of the child-care robot of the third embodiment of the present invention.

According to a third embodiment of the present invention, the robot is provided with a video screen 61 on its front side, as shown in FIG. 9. A block diagram of the robot of FIG. 9 is shown in FIG. 10. A video processor 60 is connected to the processor 16 to process a stored or received parent's image and displays it on the video screen 61.

Figure 11:
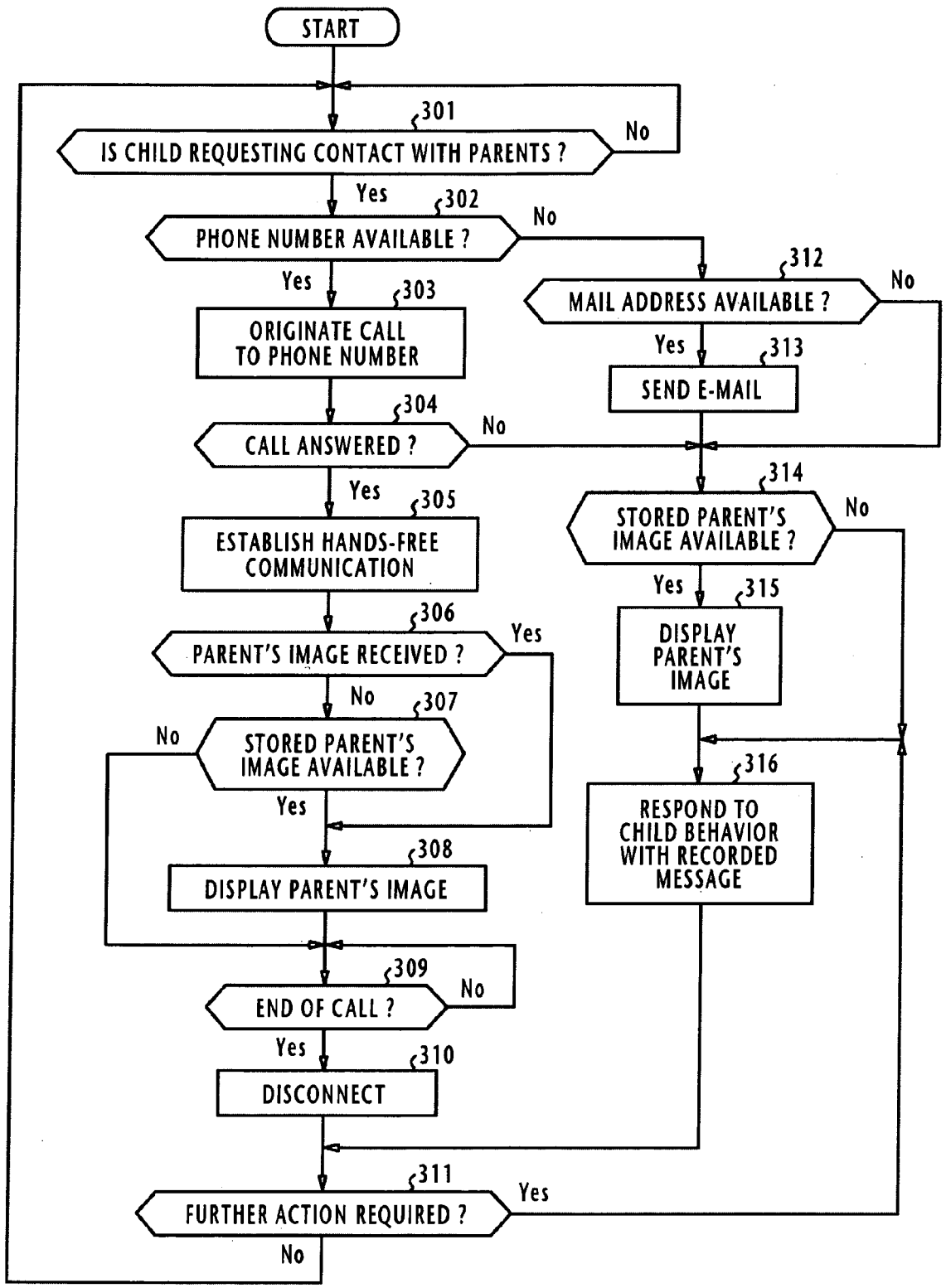
FIG. 11 is a flowchart of the operation of the processor of FIG. 10 triggered in response to a child behavior.

The operation of the processor 16 of FIG. 10 proceeds according to the flowchart of FIG. 11, in which the trigger event is a request from children to establish contact with parents.

The program routine begins with step 301 by checking to see if a child is requesting contact with parents. If so, flow proceeds to step 302 to examine the parents data memory 34 and determine if a phone number is available. If a phone number is available, a call is originated (step 303). If the call is answered (step 304), a hands-free speech communication is established between the requesting child and the parent (step 305). If a parent's image is received (step 306) or a stored parent image is available (step 307), it is displayed (step 308). When the call is terminated (step 309), the processor 16 disconnects the call (step 310). If a further action is required for a child's behavior (step 311), flow proceeds to step 316 to respond to the child's behavior with a recorded cheerful message to attract child's attention. Step 316 is repeated until no further action is required (step 311), whereupon flow returns to step 301 to repeat the above process.

If the child is still weeping, for example, after contacting the parent by the telephonic conversion, decision step 311 checks to see if the child's problem has been resolved. If not, it is determined that a further action needs to be performed and flow proceeds to step 316.

If no phone number is available (step 302), the parents data memory 34 is checked for a mail address (step 312). If a mail address is available, an e-mail is transmitted to the parent's terminal or the parent's mobile phone for advising the parent that the child is requesting a parent's telephone call (step 313).

At step 314, which is executed if the call was not answered (step 304) or if no mail address was found to be available (step 312), or when an e-mail was sent (step 313), the processor 16 checks to see if a stored parent's image is available. If so, the parent's image is displayed (step 315) to soothe the child's feeling and flow proceeds to step 316 to respond to the child behavior. Step 316 is also executed if no stored parent's image is available at step 314.

Figure 12:
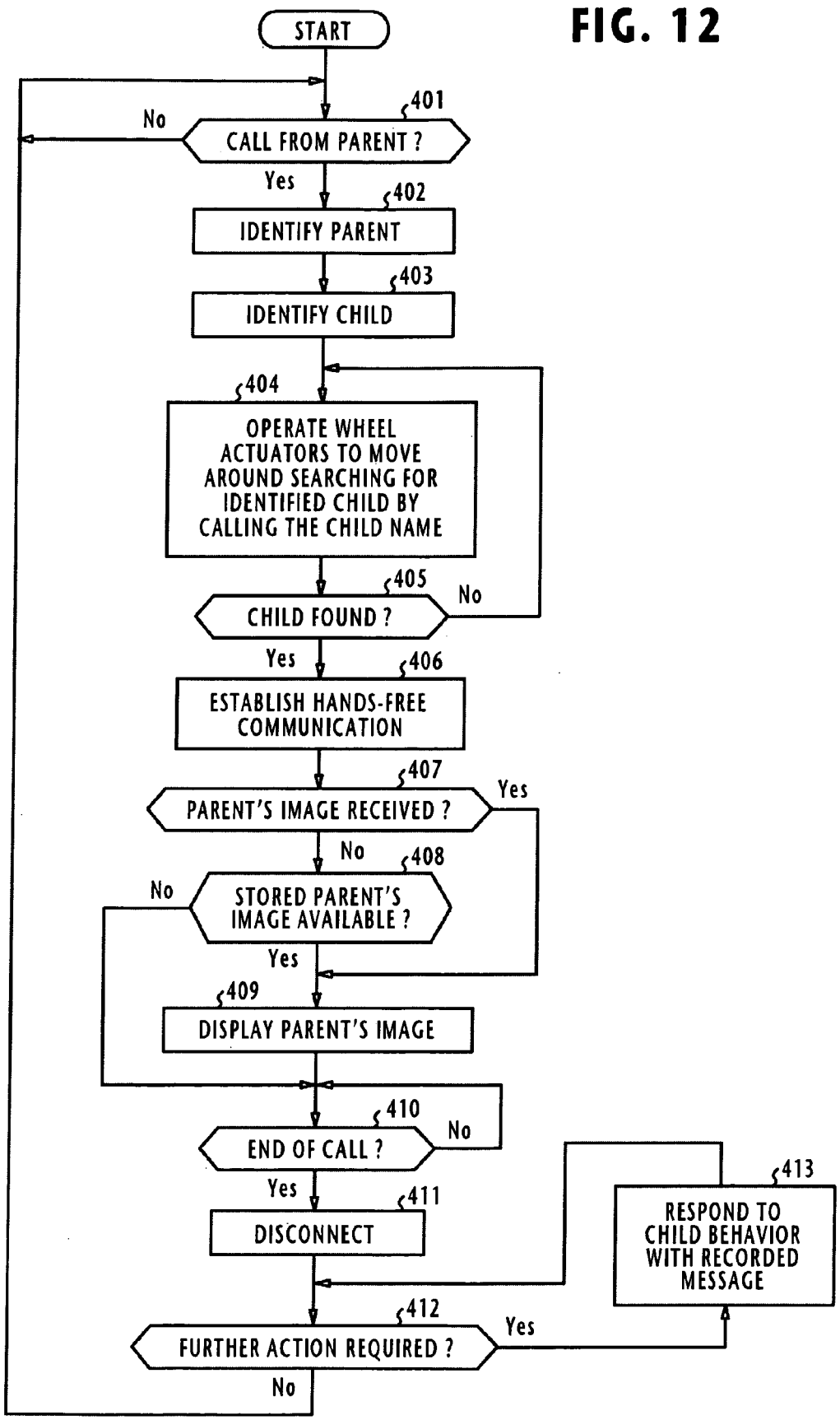
FIG. 12 is a flowchart of the operation of the processor of FIG. 10 triggered in response to a phone call from a parent.

The operation of the processor 16 of FIG. 10 will be further described with reference to the flowchart of FIG. 12, in which the trigger event is the arrival of a phone call from a parent.

The program routine begins with step 401. If a phone call is received from a parent, flow proceeds to step 402 to identify the parent using the parents data memory 34 and identify the parent's child (step 403) using the children data memory 31. At step 404, the processor 16 operates the wheel actuators to move the robot around in search of the identified child while loudly calling the child's name until the child is found (step 405). When the child is found, a hands-free speech communication is established between the parent and the child (step 406). If a parent's image is received (step 407) or a stored parent's image is available (step 408) if it is determined that no parent image is received, the available parent's image is displayed (step 409). When the call is terminated (step 410), the call is disconnected (step 411) and a check is made if a further action is required (step 412). If so, flow proceeds to step 413 to respond to the child behavior with a recorded cheerful message and then returns to step 412. Step 413 is repeated until step 412 yields a negative decision, whereupon flow returns to step 401 to repeat the above process.

Figure 13:
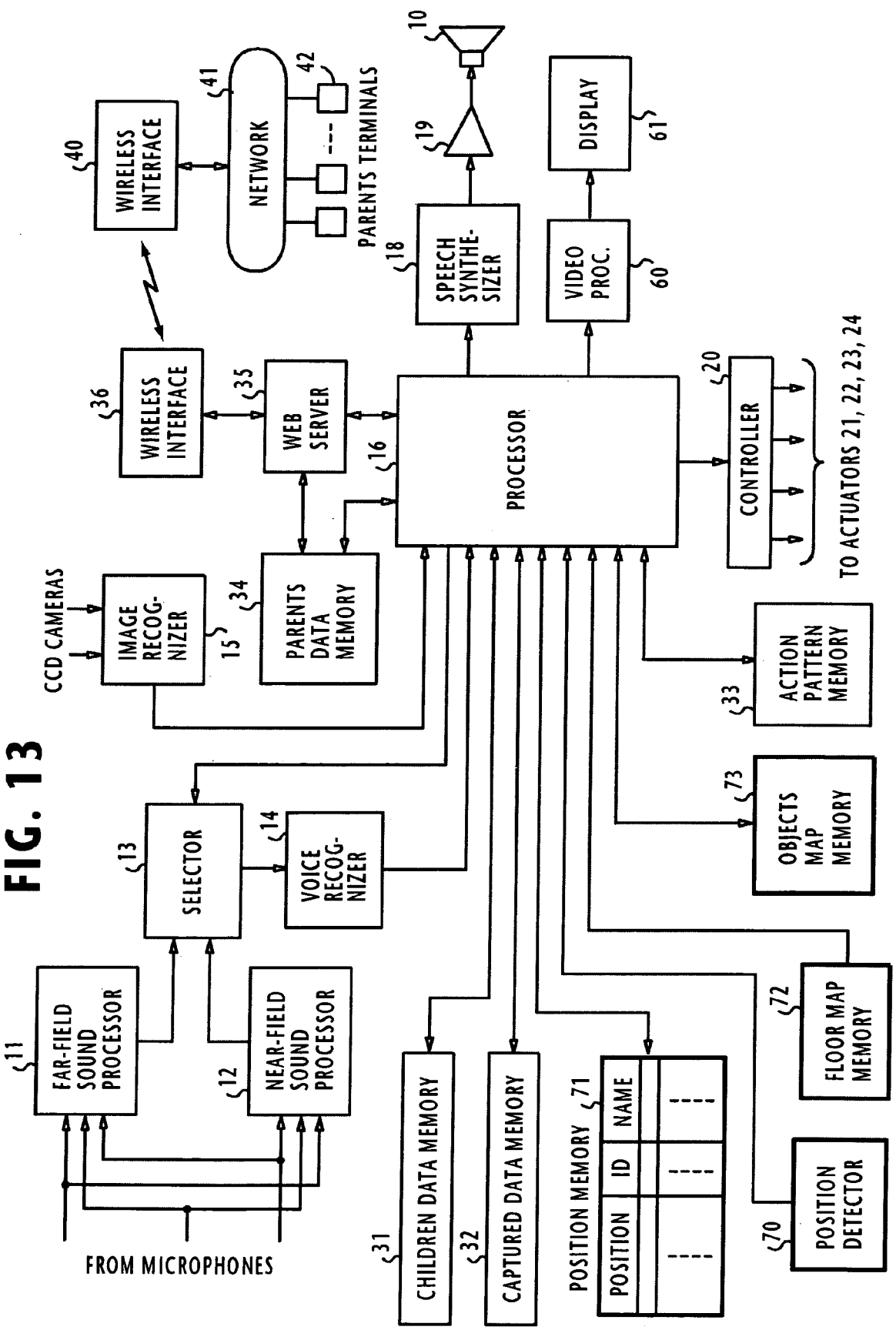
FIG. 13 is a block diagram of the child-care robot of a fourth embodiment of the present invention.

According to a fourth embodiment of the present invention, the robot of the present invention is modified as shown in FIG. 13 to include a position detector 70, a position memory 71, a floor map memory 72 and an objects location memory 73, all of which are connected to the processor 16.

Position detector 70 may be a GPS position detector for detects the geographic positions of children and teachers in the nursery school, and the position of the robot itself.

The processor 16 is programmed to move the robot in the nursery school to capture image and voice patterns of children and teachers and associates the captured patterns with their names and identification numbers, and detects their geographic positions with respect to the position of the robot. Then, the processor 16 maps the names and identification numbers of the children and teachers to the detected geographic positions in a position memory 71. Instead of GPS system, a number of wireless position sensing IC tags may be provided in strategic points of the nursery school. The robot is provided with a wireless IC tag for detecting its position with respect to each of the position sensing IC tags. A floor map memory 72 is provided for storing a floor layout of the nursery school.

Processor 16 is programmed to use the position memory 71 and the floor map memory 72 to place the stored objects (children and teachers) of position memory 71 on a floor layout retrieved from the floor map memory 72 and produce a children/teachers map in an objects map memory 73.

As described previously, when a call is received from a parent expressing a concern for her child, the processor 16 locates the position of the child using the children/teachers map stored in the objects map memory 73 and quickly moves the robot to the location of the child to obtain the child's image and voice for transmission to the requesting parent. In this way, there is no need for moving the robot in search of a target child. By constantly updating the children/teachers map and putting it on display, the teachers can recognize the locations of all children on a substantially real-time basis. This serves as an instant aid for teachers to report current conditions of the children when they receive a phone call from the parents. Additionally, the processor 16 is programmed to detect when an emergent situation occurs on a child end use the map to locate the nearest position of a teacher and dispatch the robot to the teacher for indicating the location of the child, so that the teacher can rush to the scene without delay.

Figure 14:
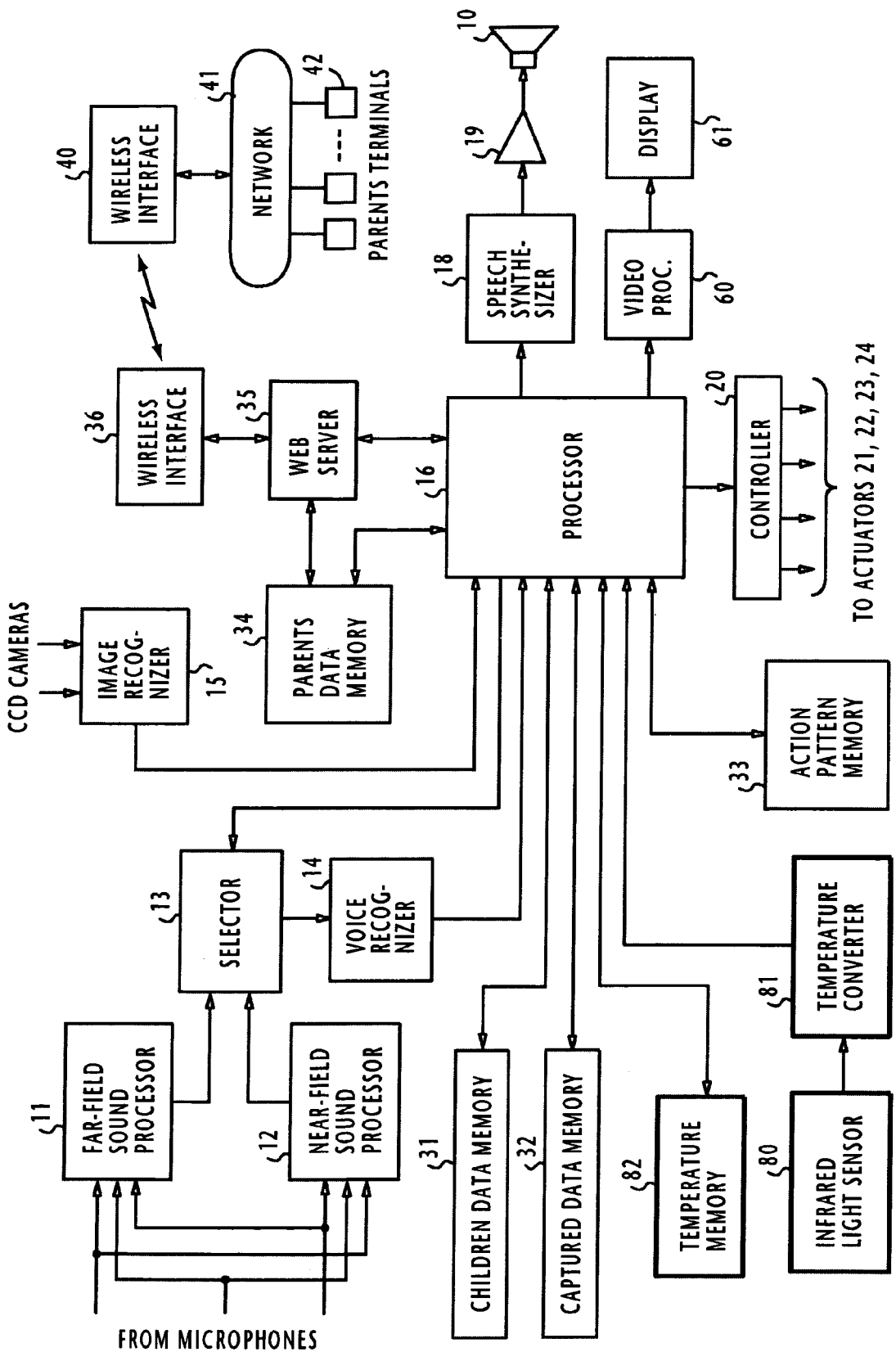
FIG. 14 is a block diagram of the child-care robot of a fifth embodiment of the present invention.

FIG. 14 is a block diagram of a fifth embodiment of the present invention in which the robot is modified to include an infrared light sensor 80, a temperature converter 81 connected to the infrared light sensor 80, and a temperature memory 82, all of which are connected to the processor 16. Children's body temperatures are monitored by moving the robot in search of target children and detecting their infrared radiations by the infrared light sensor 80 and converting the radiation levels to corresponding temperatures by the converter 81.

Figure 15:
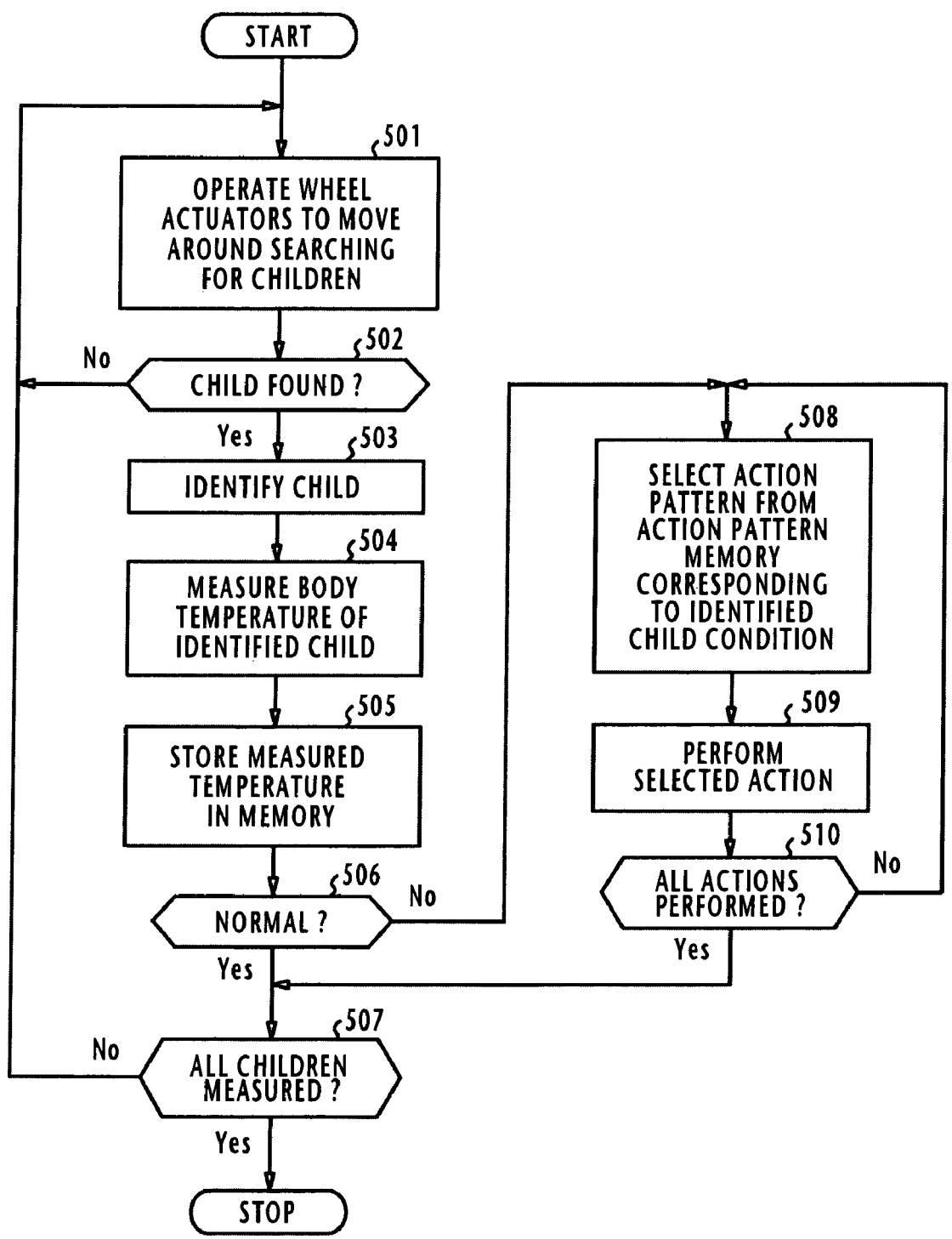
FIG. 15 is a flowchart of the operation of the processor of FIG. 14.

The operation of the processor 16 of FIG. 14 proceeds according to the flowchart of FIG. 15.

At step 501, the processor 16 operates the wheel actuators to move the robot around in search of target children If a target child is detected (step 502), the processor 16 identifies the child using the children data memory 31 (step 503) and measures the body temperature of the identified child (step 504). The detected body temperature is stored in the temperature memory 83 with data indicating the time of day at which the temperature was measured and associated with the identification number of the subject child (sep 505). At step 506, the stored temperature is compared with a range of normal temperatures. If the temperature is higher than the normal range, flow proceeds to step 508 to select an action pattern from the action pattern memory 33 corresponding to the identified child condition and the selected action pattern is performed (step 509). If the temperature of a child is higher than 38 degrees centigrade, the processor 16 consults the action pattern memory 33 to select corresponding action patterns. The actions taken in this case include "informing the parents" and "informing the teachers". If all actions necessary for the current condition of the child are performed, flow proceeds to step 507. Otherwise, flow returns to step 508 to select the next action. When the above process is not performed on all target children, flow returns from step 507 to step 501.

What is claimed is:

1. A child-care robot comprising:
   memory means for associating a plurality of child behavior patterns with a plurality of robot action patterns and associating a plurality of child identities with said plurality of child behavior patterns;
   sensor means for acquiring a child behavior pattern when a child behaves in a specified pattern;
   processor means for selecting one of said robot action patterns which is associated in said memory means with said acquired child behavior pattern; and
   acting means for performing the selected robot action pattern,
   wherein said acting means includes communication means for establishing a communication channel to a remote terminal via a communications network,
   wherein said acquired child behavior pattern indicates a request from a child for communication with a parent of the child,
   wherein said memory means further associates a plurality of parents terminals to said plurality of child identities, and
   wherein said communication means identifies one of said parents terminals which is associated with the identity of said child as said remote terminal in response to said request.

2. The child-care robot of claim 1, further comprising a robot housing in which said memory means, said sensor means, said processor means and said acting means are provided inside said robot housing.

3. The child-care robot of claim 1, further comprising:
   a robot housing in which said sensor means, said processor means and said acting means are provided inside said housing;
   first wireless communication means in said robot housing; and
   second wireless communication means in a fixed location for establishing a wireless link with said first wireless communication means, wherein said memory means is provided in said fixed location so that said processor means is accessible to the memory means via said wireless link.

4. The child-care robot of claim 3, wherein said second wireless communication means comprises a wireless LAN.

5. The child-care robot of claim 1, wherein said plurality of child behavior patterns includes a plurality of image patterns.

6. The child-care robot of claim 1, wherein said plurality of child behavior patterns include a plurality of voice patterns.

7. The child-care robot of claim 1, wherein said communication means transmits an image or voice of said child to said remote terminal.

8. The child-care robot of claim 1, wherein said communication means includes a loudspeaker for reproducing a voice signal transmitted from said remote terminal.

9. The child-care robot of claim 8, wherein said communication means includes a screen for displaying a video signal transmitted from said remote terminal.

10. The child-care robot of claim 8, wherein said memory means includes a plurality of entries corresponding to said plurality of child behavior patterns, each of said entries including a plurality of prioritized robot actions, and wherein said processor means identifies one of said entries of the memory means corresponding to said acquired child behavior pattern and detects each of the prioritized robot actions of the identified entry in descending order of priority if one of the robot actions is not successfully performed by said acting means.

11. The child-care robot of claim 1 wherein said communication means is responsive to an inquiry message from said remote terminal for transmitting an image or a voice of said child to said remote terminal.

12. The child-care robot of claim 11, wherein said memory means comprises a parents data memory for associating a plurality of parent identities with a plurality of child identities, wherein said processor means is responsive to said inquiry message for detecting a parent identity from said parents data memory and detecting the child identity of said child associated with the detected parent identity, wherein said sensor means is responsive to the detection of the child identity by said processor means for acquiring an image or a voice of the identified child, wherein said communication means transmits the acquired image or voice to said remote terminal.

13. The child-care robot of claim 1, wherein said acting means comprises means for moving the robot around an area according to a control signal from said processor means.

14. The child-care robot of claim 13, wherein said sensor means comprises means for measuring a body temperature of said child, and wherein said processor means controls said moving means to move the robot around said area in search of a plurality of children to enable said temperature measuring means to measure the body temperature of each of the children.

15. The child-care robot of claim 13, wherein said temperature measuring means comprises an infrared light sensor for detecting infrared radiation from each of said children and means for converting the detected infrared radiation to the measured body temperature of each of said children.

16. The child-care robot of claim 1, further comprising position detector means for detecting a plurality of geographic positions of objects, wherein said memory means comprises:

a position memory for associating said detected geographic positions of objects with a plurality of identities of the objects; and a map memory, wherein said processor means is configured to create a map in said map memory for indicating said geographic positions of said objects and said identities of the objects on a floor layout of an architecture.

17. The child-care robot of claim 16, wherein said objects are children, and wherein said position detector means detects said plurality of geographic positions of said children when said robot is moving around said area in search of said children.

18. The child-care robot of claim 16, wherein said objects are nursery school teachers, and wherein said position detector means detects said plurality of geographic positions of said teachers when said robot is moving around said area in search of said teachers.

19. The child-care robot of claim 16, wherein said moving means moves the robot around said area in search of an object according to the geographic position of the object indicated in said map memory.

20. The child-care robot of claim 1, wherein said sensor means comprises a voice recognizer for producing a voice pattern as said child behavior pattern from a recognized voice of said child.

21. The child-care robot of claim 20, wherein said memory means comprises:

a children data memory for associating a plurality of voice patterns with a plurality of child behavior patterns, and wherein said processor means is configured to identify one of said child behavior patterns associated with the voice pattern produced by said voice recognizer and detect said one robot action associated with the identified child behavior pattern.

22. The child-care robot of claim 1, wherein said sensor means comprises means for measuring a body temperature of said child to produce a temperature indicating signal as said child behavior pattern identified child behavior pattern.

23. The child-care robot of claim 22, wherein said memory means comprises a temperature memory for associating the measured temperature with said child and data indicating time of day at which the temperature is measured.

24. The child-care robot of claim 22, wherein said processor means determines whether the measured temperature is higher than a predetermined, and wherein said communication means communicates an unfavorable condition of said child to one of a nearby caretaker and said remote terminal when said processor determines that the measured temperature is higher than said predetermined value.

25. A method of controlling a child-care robot, comprising:

associating a plurality of child behavior patterns with a plurality of robot action patterns and a plurality of child identities with said plurality of child behavior patterns and a plurality of parents terminals to said plurality of child identities;

acquiring a child behavior pattern when a child behaves in a specified pattern, wherein said acquiring step includes acquiring a child behavior pattern that indicates a request from a child for communication with a parent of the child;

selecting one of said robot action patterns which is associated with said acquired child behavior pattern; and performing the selected robot action pattern, wherein said performing step includes identifying one of said plurality of parents terminals which is associated with the identity of said child as a remote terminal and establishing a communication channel to said remote terminal via a communications network in response to said request from said child.

26. A non-transitory computer-readable storage medium containing a program for controlling a child-care robot, said program comprising the steps of:

associating a plurality of child behavior patterns with a plurality of robot action patterns and a plurality of child identities with said plurality of child behavior patterns and a plurality of parents terminals to said plurality of child identities;

acquiring a child behavior pattern when a child behaves in a specified pattern, wherein said acquiring step includes acquiring a child behavior pattern that indicates a request from a child for communication with a parent of the child;

selecting one of said robot action patterns which is associated with said acquired child behavior pattern; and performing the detected robot action pattern, wherein said performing step includes identifying one of said plurality of parents terminals which is associated with the identity of said child as a remote terminal and establishing a communication channel to said remote terminal via a communications network in response to said request from said child.

* * * * *